United States Patent
Moreau et al.

(10) Patent No.: US 11,020,344 B2
(45) Date of Patent: Jun. 1, 2021

(54) AURICULAR CLEANING COMPOSITION

(71) Applicant: Vetoquinol SA, Magny-Vernois (FR)

(72) Inventors: Marinette Moreau, Saint-Germain (FR); Aurelie Brevet, Lure (FR); Elodie Lego, Lure (FR)

(73) Assignee: VETOQUINOL SA, Lure (FR)

( * ) Notice: Subject to any disclaimer, the term of this patent is extended or adjusted under 35 U.S.C. 154(b) by 0 days.

(21) Appl. No.: 15/765,044

(22) PCT Filed: Sep. 29, 2016

(86) PCT No.: PCT/FR2016/052496
§ 371 (c)(1),
(2) Date: Mar. 30, 2018

(87) PCT Pub. No.: WO2017/055762
PCT Pub. Date: Apr. 6, 2017

(65) Prior Publication Data
US 2020/0337992 A1    Oct. 29, 2020

(30) Foreign Application Priority Data
Sep. 30, 2015  (FR) ...................................... 1559298

(51) Int. Cl.
| | | |
|---|---|---|
| A61K 9/00 | (2006.01) | |
| A61P 27/16 | (2006.01) | |
| A61K 47/10 | (2017.01) | |
| A61K 47/12 | (2006.01) | |
| A61K 47/14 | (2017.01) | |
| A61K 31/16 | (2006.01) | |
| A61K 36/28 | (2006.01) | |

(52) U.S. Cl.
CPC ............ *A61K 9/0046* (2013.01); *A61K 47/10* (2013.01); *A61K 47/12* (2013.01); *A61K 47/14* (2013.01); *A61P 27/16* (2018.01); *A61K 31/16* (2013.01); *A61K 36/28* (2013.01)

(58) Field of Classification Search
None
See application file for complete search history.

(56) References Cited

U.S. PATENT DOCUMENTS

| | | |
|---|---|---|
| 3,422,186 A | 1/1969 | Sasmor |
| 4,895,875 A | 1/1990 | Winston |
| 5,296,472 A | 3/1994 | Sanchez et al. |
| 5,380,711 A | 1/1995 | Sanchez et al. |
| 5,480,658 A | 1/1996 | Melman |
| 6,579,543 B1* | 6/2003 | McClung ............. A61K 36/886 424/728 |
| 2004/0131660 A1* | 7/2004 | Lange .................. A61K 8/0208 424/443 |
| 2009/0318558 A1 | 12/2009 | Kim et al. |
| 2012/0328525 A1* | 12/2012 | Edelson ................. A61K 8/375 424/9.2 |
| 2017/0216439 A1* | 8/2017 | Lebel ....................... A61K 9/06 |

FOREIGN PATENT DOCUMENTS

| | | |
|---|---|---|
| KR | 20110019327 A | 2/2011 |
| WO | 2008110741 A2 | 9/2008 |

OTHER PUBLICATIONS

Hawke, M., "Update on cerumen and cerumenolytics", Ear Nose & Throat Journal, Aug. 2002, vol. 81, Suppl 1; pp. 23-24.
International Search Report for International Application No. PCT/FR2016/052496; International filing date: Sep. 29, 2016; dated Feb. 7, 2017.
Jacobson, L.S., "Diagnosis and medical treatment of otitis externa in the dog and cat", S. Afr. vet.Ass. Dec. 2002 vol. 73 No. 4; pp. 162-170.
Malard, O., et al., "Pathologic acquise de l'oreille externe" ("Acquired diseases of the external ear"] EMC-Oto-rhino-laryngologie, 2 (2005); pp. 263-289 (with English Title and abstract).
Extra Strength Cold/Hot Pain Relief, Patch, Aug. 1, 2000, downloaded from online Mintel Datase GNPD, www.GNPD.com, Acc. No. 839715, NPL ref XP-0027-57636 (2 pages).
Warming Cream, Nov. 2008; downloaded from online Mintel Datase GNPD, www.GNPD.com, Acc. No. 991517 NPL ref X-002757635 (2 pages).
Nielloud, et al, P-75 Development of an in vitro test to evaluate cerumen-dissolving properties of veterinary ear cleansing solutions, Veterinary Dermatology, 2004, 15, (suppl.1); p. 65.
Sanchez-Leal, et al., "In vitro investigation of cerumenolytic activity of various otic cleaners for veterinary use", Veterinary Dermatology, vol. 17, No. 2, Apr. 2006, pp. 121-127.
Silverstein, Herbert et al.,"A prospective study to evaluate the efficacy of isopropyl alcohol irrigations to prevent cerumen impaction", Ear, Nose, & Throat Journal Mar. 2012, vol. 91, No. 3; pp. E25-E28.
Written Opinion of the International Searching Authority for International Application No. PCT/FR2016/052496; International filing date: Sep. 29, 2016; dated Feb. 7, 2017.

* cited by examiner

*Primary Examiner* — Celeste A Roney
(74) *Attorney, Agent, or Firm* — Cantor Colburn LLP

(57) ABSTRACT

An auricular cleaning composition includes isopropylic alcohol and/or diethylene glycol monoethyl ether as ceruminolytic agent(s), optionally in combination with caprylocaproyl polyoxyl-8 glyceride.

11 Claims, 6 Drawing Sheets

AURICULAR CLEANING COMPOSITION

This application claims priority to International Application No. PCT/FR2016/052496 filed Sep. 29, 2016 and to French Application No. 1559298 filed Sep. 30, 2015; the entire contents of each are incorporated herein by reference.

DESCRIPTION

Technical Field

The technical field of the present invention relates to auricular cleaning compositions for human or animal use.

The present invention relates more specifically to an auricular cleaning composition comprising isopropyl alcohol and/or diethylene glycol monoethyl ether as cerumenolytic agent(s), optionally in combination with caprylcaproyl polyoxyl-8 glyceride.

In the description below, the references between square brackets [ ] refer to the list of references presented at the end of the text.

Background Art

External otitis in dogs is a common pathological condition. The treatment thereof requires good knowledge of the physiopathology of this disease in order to propose specific cleaning according to the clinical examination. Numerous auricular cleaners are currently available in France and overseas. They contain several active ingredients and excipients, and do not require marketing authorization.

The objective of auricular cleaning is to remove the excess cerumen, in order to make the surface of the epidermis which coats the external ear accessible to the medical treatment.

Cerumenolytic agents are commonly used in auricular cleaners for dissolving cerumen. There are two types: cerumenolytics in the strict sense, which break the integrity of cerumen by lysing the agglomerate of squames, and simple lubricants which have a limited cerumen-softening and discharging action. A cerumenolytic is supposed to break the linkage between the corneocytes, and thus to soften, liquefy and/or dissolve the cerumen. It weakens the membrane of the corneocytes and, by virtue of an osmotic gradient, allows the passage of water and the fragmentation of these cells. Their aim is also to break the adhesions between the plug and the wall of the canal (Hawke, 2002 [1]).

Sodium docusate, sodium bicarbonate, aqueous hydrogen peroxide, and urea peroxide are cerumenolytic products commonly used in human medicine (Malard et al. 2005 [2]). Carbamide peroxide, polysorbate 80, sodium lauryl sulfate and xylene are also molecules with cerumenolytic properties.

In addition, some other agents have been reported as being somewhat effective in softening ear wax. Such agents include glycerin (glycerol), olive oil, almond oil, mineral oil, sodium carbonate and dichlorobenzene. After softening with one of these agents, irrigation with water at body temperature or physiological saline is often carried out in order to remove the softened cerumen. Dichlorobenzene sometimes results in irritation of the ear canal.

Compositions which facilitate the cleaning of ear wax have also been the subject of several patents. For example, patent U.S. Pat. No. 3,422,186 (Sasmor, [3]) describes cerumenolytic compositions comprising ethylene oxide/polyoxypropylene glycol condensates. Patent U.S. Pat. No. 4,895,875 (Winston, [4]) describes stabilized peroxide solutions comprising urea peroxide and glycerin, and the use thereof for removing cerumen. Patent U.S. Pat. No. 5,296,472 (Sanchez et al, [5]) describes compositions comprising cyclodextrins and methods of use for removing cerumen. Patent U.S. Pat. No. 5,380,711 (Sanchez et al, [6]) describes "empty" cyclodextrin-based oil-free compositions and methods of use for removing cerumen. In addition, patent U.S. Pat. No. 5,480,658 (Melman, [7]) describes aqueous compositions comprising acetic acid and boric acid for cleaning the external ear canal of domestic animals.

An aqueous 5% sodium bicarbonate solution is often prepared and used by physicians for treating cerumen plugs. This solution can be prepared with or without glycerin. However, these solutions are not stable and, as a result, sodium bicarbonate solutions have never been developed in "ready-to-use" commercial products.

There is therefore a need for an improved composition which makes it possible to efficiently remove cerumen, which is commercially viable and which does not suffer from the limitations of the currently available cerumenolytics.

SUMMARY OF THE INVENTION

An objective of the present invention is specifically to meet these needs and to provide a response to the drawbacks known in the art by providing an auricular cleaning composition comprising:

isopropyl alcohol and/or diethylene glycol monoethyl ether as cerumenolytic agent(s), optionally in combination with caprylcaproyl polyoxyl-8 glyceride; and optionally an otologically acceptable aqueous carrier.

There are two types of cerumenolytic solutions: aqueous solutions and oily solutions. The aqueous solutions may be preferred to the oily solutions for two reasons. First, the aqueous solutions are discharged more easily from the canal and therefore allow faster cleaning and drying. Furthermore, the oily solutions form an occlusive film and, if they are not well discharged, promote the development of bacteria. Thus, advantageously, the auricular cleaning composition according to the invention is a non-oily solution, and contains an aqueous carrier.

The composition can contain any excipient conventionally used in auricular cleaning compositions, such as:

drying agents which dry the surface of the ear canal in order to prevent the phenomenon of maceration that can promote bacterial proliferation, anti-seborrheics, emollients, antiseptics, anti-inflammatories or soothing agents, fragrances, etc.

Thus, the composition according to the invention can also comprise an anti-seborrheic agent, an emollient, a surfactant, a buffering agent, an antiseptic agent, an anti-inflammatory agent (or soothing agent) and/or a preservative.

Among the anti-seborrheic agents that can be used in the context of the invention, mention may be made, for example, of lipoamino acids such as capryloyl glycine ("Lipacide C8G®") or undecylenoyl glycine ("Lipacide UG®"), or a mixture thereof.

Among the emollients that can be used in the context of the invention, mention may be made, for example, of glycerin, propylene glycol, polyethylene glycol, triacetin, silicone derivatives (for example: dimethicone), polyols or a mixture of at least two thereof.

Among the surfactants that can be used in the context of the invention, mention may be made, for example, of polysorbates such as polyoxyethylene sorbitan monooleate, 4-(1,1,3,3-tetramethylbutyl)phenol/poly(oxyethylene) polymers, poly(oxyethylene)-poly(oxypropylene) block copolymers, polyethylene glycol esters of fatty acids, polyoxypropylene ethers of $C_{12}$ to $C_{18}$ alkanes, or a mixture of at least two thereof. Preferably, they may be polysorbates such as polyoxyethylene sorbitan monooleate, poly(oxyethylene)-poly(oxypropylene) block copolymers, polyethylene glycol esters of fatty acids, polyoxypropylene ethers of $C_{12}$ to $C_{18}$ alkanes, or a mixture of at least two thereof.

Among the buffering agents that can be used in the context of the invention, mention may be made, for example, of trishydroxymethylaminomethane (or 2-amino-2-hydroxymethylpropane-1,3-diol, or "tromethamine"), citrate, phosphate, borate, acetate, sodium hydroxide, glycine, triethanolamine, salts thereof, or a mixture of at least two thereof.

As used herein, the term "borate" or "boric acid" refers to an inorganic compound comprising boron and one or more oxygen groups, and which is either in acid form or in basic form when it is dissolved in a composition of the present invention. The sources of borate/boric acid compounds comprise alkaline metal salts of borate, boric acid and borax. The borate/boric acid compound can also contribute to the antimicrobial preservation of the compositions of the present invention at a level that is effective for multi-use dispensing. The solubility of the borate/boric acid compounds in water may be limited. However, the solubility of these compounds can be increased by adding, for example, a monomeric or polymeric polyol.

As used herein, the term "monomeric polyol" refers to a compound having 2 to 6 carbon atoms and at least two hydroxyl groups. Examples of monomeric polyols include glycerin, propylene glycol, ethylene glycol, sorbitol and mannitol. Preferably, the monomeric polyols are selected from polyols having 2-3 carbon atoms and at least two hydroxyl groups, such as glycerin, 1,2-propanediol ("propylene glycol"), 1,3-propanediol and ethylene glycol. For example, the monomeric polyol may be glycerin.

As used herein, the term "polymeric polyol" refers to a polyalkoxylated glycol having a molecular weight ranging from approximately 200 to 600 Daltons. Examples of polymeric polyols include polyethylene glycol 200 (denoting a molecular weight of 200 daltons, "PEG 200") and PEG 400. The PEG can optionally be monoalkoxylated. Examples of monoalkoxylated PEGs comprise monomethoxy PEG 200 and ethoxy PEG 400. Although these alkoxylated PEGs are not technically polyols, they have a structure similar to non-alkoxylated PEGs. Consequently, for the purposes of the definition, they are included in the expression "polymeric polyol".

Among the antiseptic agents that can be used in the context of the invention, mention may be made, for example, of a calendula (marigold) extract and the antiseptics of the biguanide family, such as chlorhexidine, or a mixture of at least two thereof.

Among the anti-inflammatory agents (or soothing agents) that can be used in the context of the invention, mention may be made, for example, of a calendula (marigold) extract.

Among the preservatives that can be used in the context of the invention, mention may be made, for example, of boric acid, poly[dimethylimino-2-butene-1,4-diyl]chloride-alpha-[4-tris(2-hydroxyethyl)ammonium] dichloride, benzalkonium halides, alexidine salts, chlorhexidine salts, or a mixture of at least two thereof.

Advantageously, the composition according to the invention may comprise diethylene glycol monoethyl ether as cerumenolytic agent. It can be used as sole cerumenolytic agent in the composition. Alternatively, diethylene glycol monoethyl ether can be used in combination with isopropyl alcohol and/or caprylcaproyl polyoxyl-8 glyceride.

For example, the composition according to the invention may comprise diethylene glycol monoethyl ether as cerumenolytic agent, in combination with caprylcaproyl polyoxyl-8 glyceride; with a diethylene glycol monoethyl ether content ranging from 10% to 40% by weight, and a caprylcaproyl polyoxyl-8 glyceride content ranging from 20% to 60% by weight; the total content of diethylene glycol monoethyl ether and caprylcaproyl polyoxyl-8 glyceride ranging from 50% to 70% by weight; the % being expressed relative to the total weight of the composition.

Alternatively, the composition according to the invention may comprise isopropyl alcohol as cerumenolytic agent, in combination with caprylcaproyl polyoxyl-8 glyceride; with an isopropyl alcohol content ranging from 5% to 20% by weight, and a caprylcaproyl polyoxyl-8 glyceride content ranging from 20% to 60% by weight; the total content of isopropyl alcohol and caprylcaproyl polyoxyl-8 glyceride ranging from 35% to 75% by weight; the % being expressed relative to the total weight of the composition.

Alternatively, the composition according to the invention may comprise diethylene glycol monoethyl ether and isopropyl alcohol as cerumenolytic agents; with a diethylene glycol monoethyl ether content ranging from 14% to 33% by weight, and an isopropyl alcohol content ranging from 20% to 40% by weight; the total content of diethylene glycol monoethyl ether and isopropyl alcohol ranging from 35% to 70% by weight; the % being expressed relative to the total weight of the composition.

Alternatively, the composition according to the invention may comprise the diethylene glycol monoethyl ether and isopropyl alcohol as cerumenolytic agents, in combination with caprylcaproyl polyoxyl-8 glyceride. Advantageously, the composition according to the invention may comprise a diethylene glycol monoethyl ether content ranging from 25% to 35% by weight, an isopropyl alcohol content ranging from 5% to 10% by weight, a caprylcaproyl polyoxyl-8 glyceride content ranging from 20% to 35% by weight; the total content of diethylene glycol monoethyl ether, isopropyl alcohol and caprylcaproyl polyoxyl-8 glyceride ranging from 60% to 70% by weight; the % being expressed relative to the total weight of the composition.

According to another aspect, the invention relates to a process for totally or partially removing cerumen, comprising a step consisting in introducing, into the external ear canal of a human or animal subject, any one of the auricular cleaning compositions according to the invention described in the present document. The appearance of cerumen in the ear is a normal phenomenon (it is not a disease or a pathological condition). The introduction of a composition according to the invention into the external ear canal of a healthy subject merely cleans the canal wall without any therapeutic effect (the health of the human or animal subject is not improved by this). It is therefore a non-therapeutic process for totally or partially removing cerumen.

The animal may be a mammal, preferably a domestic animal such as a dog or a cat.

The inventors have discovered that Transcutol® (2-(2-ethoxyethoxy)ethanol, or ethoxydiglycol, or diethylene glycol monoethyl ether) has a cerumenolytic effect, and that this effect is potentiated with Labrasol® (caprylcaproyl polyoxyl-8 glyceride).

The inventors have also discovered that the cerumenolytic effect of isopropyl alcohol is also potentiated with Labrasol® (caprylcaproyl polyoxyl-8 glyceride).

Thus, according to another aspect, the invention relates to the use of isopropyl alcohol and/or of diethylene glycol monoethyl ether as cerumenolytic agent(s). In the same way as for the abovementioned process for removing cerumen, it is a non-therapeutic use, the production of cerumen in the human or animal ear being a normal (non-pathological) phenomenon.

According to another aspect, the invention relates to the use of isopropyl alcohol and/or of diethylene glycol monoethyl ether as cerumenolytic agent(s) in the preparation of a composition intended to totally or partially remove cerumen, in particular in animals.

According to another aspect, the invention relates to the use of caprylcaproyl polyoxyl-8 glyceride as agent for potentiating the cerumenolytic effect of isopropyl alcohol and/or of diethylene glycol monoethyl ether in an auricular cleaning composition. Thus, according to one aspect, the invention relates to a process for potentiating the cerumenolytic effect of isopropyl alcohol and/or of diethylene glycol monoethyl ether in an auricular cleaning composition, comprising the addition of an effective amount of caprylcaproyl polyoxyl-8 glyceride to the composition.

Most particularly, the present invention relates to the use of the combination of isopropyl alcohol and/or of diethylene glycol monoethyl ether as cerumenolytic agent(s), with caprylcaproyl polyoxyl-8 glyceride. Thus, according to one aspect, the invention relates to a process for totally or partially removing cerumen, comprising a step consisting in introducing, into the external ear canal of a human or animal subject, a composition combining isopropyl alcohol and/or diethylene glycol monoethyl ether as cerumenolytic agent(s), with caprylcaproyl polyoxyl-8 glyceride.

The present invention also relates to the use of the combination of isopropyl alcohol with diethylene glycol monoethyl ether as cerumenolytic agents. Thus, the present invention also relates to a process for totally or partially removing cerumen, comprising a step consisting in introducing, into the external ear canal of a human or animal subject, a composition combining isopropyl alcohol with diethylene glycol monoethyl ether as cerumenolytic agents.

The present invention also relates to the use of the triple combination of isopropyl alcohol with diethylene glycol monoethyl ether as cerumenolytic agent(s), and caprylcaproyl polyoxyl-8 glyceride. Thus, the present invention also relates to an auricular cleaning composition comprising the triple combination of isopropyl alcohol with diethylene glycol monoethyl ether as cerumenolytic agents, in combination with caprylcaproyl polyoxyl-8 glyceride.

Other advantages will become apparent to those of ordinary skill in the art upon reading the examples below, with reference to the appended figures, all of which are given by way of illustration and are non-limiting.

| | |
|---|---|
| 1 | 100% isopropyl alcohol |
| 2 | 100% Transcutol ® |
| 3 | 100% Labrasol ® (batch 140734) |

Figure 2:
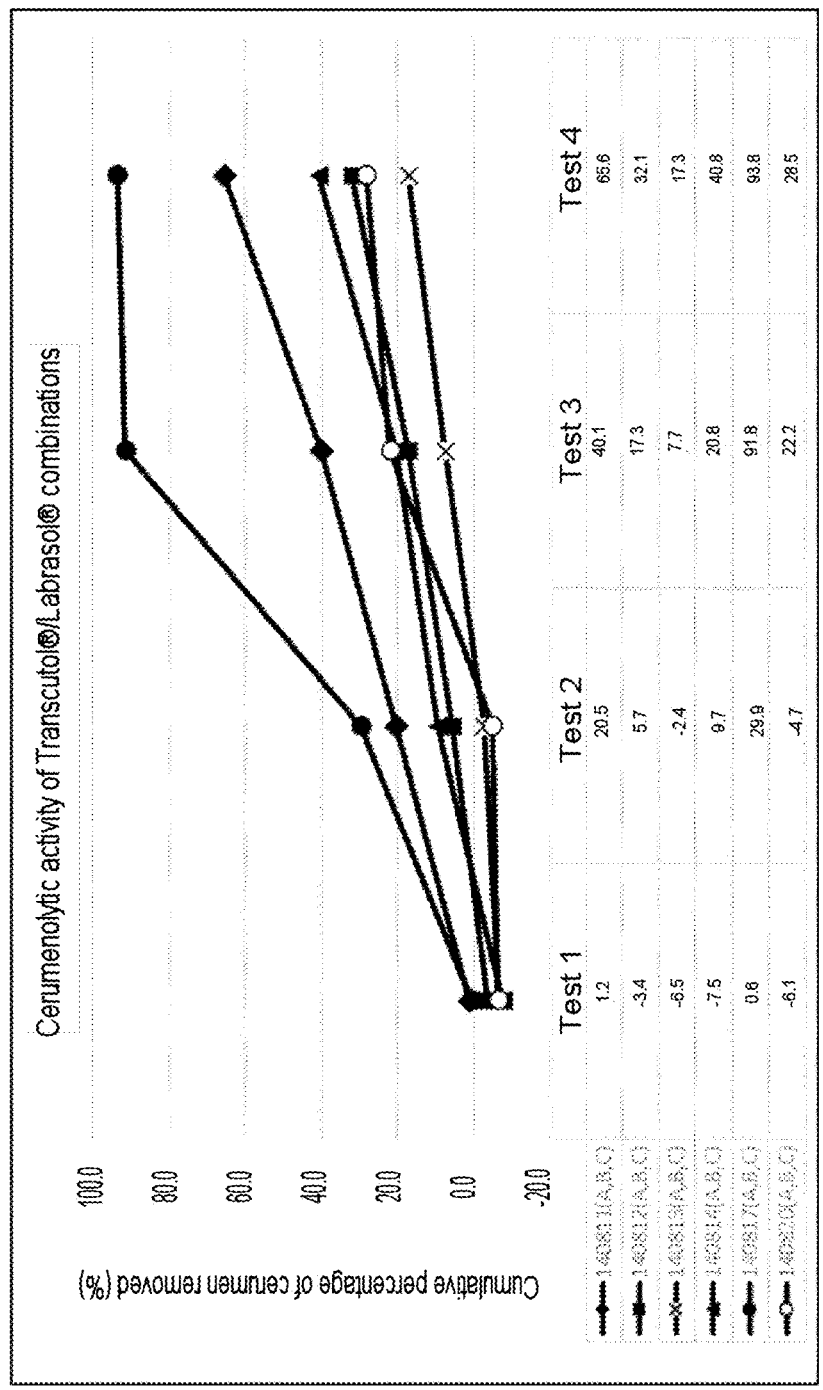

FIG. 2: Graph representing the cerumenolytic effect of the auricular cleaning compositions based on the Transcutol®/Labrasol® combination:

| | |
|---|---|
| 1 | 140811: 30% Transcutol ®, 40% Labrasol ®, 2% Tween 80 ®, 17.0% Water, 1% Lipacide C8G ®, 1% Lipacide UG ®, 1% Tromethamine, 5% Glycerin, 3% *Calendula* |
| 2 | 140812: 30% Transcutol ®, 30% Labrasol ®, 2% Tween 80 ®, 27.0% Water, 1% Lipacide C8G ®, 1% Lipacide UG ®, 1% Tromethamine, 5% Glycerin, 3% *Calendula* |
| 3 | 140813: 30% Transcutol ®, 20% Labrasol ®, 2% Tween 80 ®, 37.0% Water, 1% Lipacide C8G ®, 1% Lipacide UG ®, 1% Tromethamine, 5% Glycerin, 3% *Calendula* |
| 4 | 140814: 20% Transcutol ®, 50% Labrasol ®, 2% Tween 80 ®, 17.0% Water, 1% Lipacide C8G ®, 1% Lipacide UG ®, 1% Tromethamine, 5% Glycerin, 3% *Calendula* |
| 5 | 140817: 40% Transcutol ®, 30% Labrasol ®, 2% Tween 80 ®, 17.0% Water, 1% Lipacide C8G ®, 1% Lipacide UG ®, 1% Tromethamine, 5% Glycerin, 3% *Calendula* |
| 6 | 140820: 10% Transcutol ®, 60% Labrasol ®, 2% Tween 80 ®, 17.0% Water, 1% Lipacide C8G ®, 1% Lipacide UG ®, 1% Tromethamine, 5% Glycerin, 3% *Calendula* |

Figure 3:
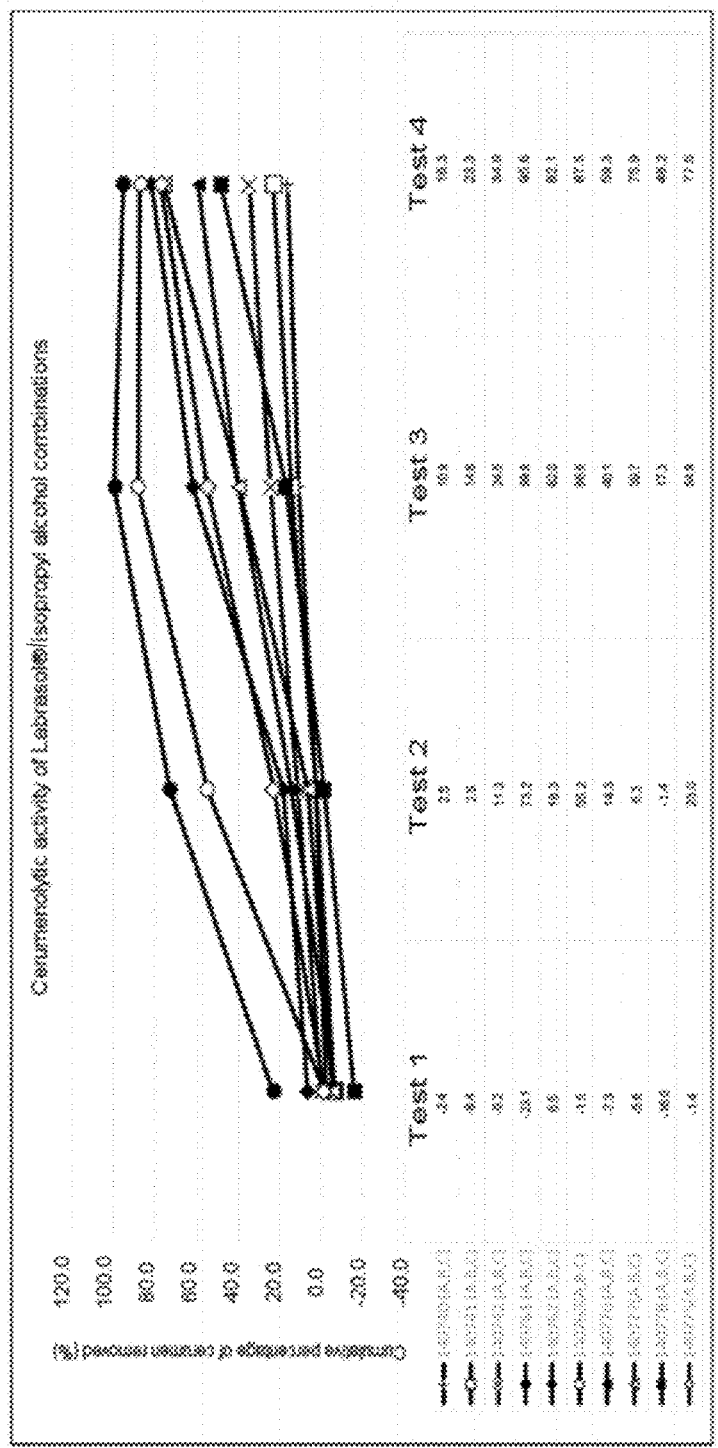

FIG. 3: Graph representing the cerumenolytic effect of the auricular cleaning compositions based on the isopropyl alcohol/labrasol combination:

| | |
|---|---|
| 1 | 140740: 15% Isopropyl alcohol, 20% Labrasol ®, 2% Tween 80 ®, 51.50% Water, 1% Lipacide C8G ®, 1% Lipacide UG ®, 1% Tromethamine, 5% Glycerin, 3% *Calendula*, 0.5% orange fragrance |
| 2 | 140741: 15% Isopropyl alcohol, 30% Labrasol ®, 2% Tween 80 ®, 41.50% Water, 1% Lipacide C8G ®, 1% Lipacide UG ®, 1% Tromethamine, 5% Glycerin, 3% *Calendula*, 0.5% orange fragrance |
| 3 | 140742: 15% Isopropyl alcohol, 40% Labrasol ®, 2% Tween 80 ®, 31.50% Water, 1% Lipacide C8G ®, 1% Lipacide UG ®, 1% Tromethamine, 5% Glycerin, 3% *Calendula*, 0.5% orange fragrance |
| 4 | 140761: 20% Isopropyl alcohol, 40% Labrasol ®, 2% Tween 80 ®, 26.50% Water, 1% Lipacide C8G ®, 1% Lipacide UG ®, 1% Tromethamine, 5% Glycerin, 3% *Calendula*, 0.5% orange fragrance |
| 5 | 140762: 15% Isopropyl alcohol, 50% Labrasol ®, 2% Tween 80 ®, 21.50% Water, 1% Lipacide C8G ®, 1% Lipacide UG ®, 1% Tromethamine, 5% Glycerin, 3% *Calendula*, 0.5% orange fragrance |
| 6 | 140763: 15% Isopropyl alcohol. 60% Labrasol ®, 2% Tween 80 ®, 11.50% Water, 1% Lipacide C8G ®, 1% Lipacide UG ®, 1% Tromethamine, 5% Glycerin, 3% *Calendula*, 0,5% orange fragrance |
| 7 | 140775: 10% Isopropyl alcohol. 50% Labrasol ®, 2% Tween 80 ®, 26.50% Water, 1% Lipacide C8G ®, 1% Lipacide UG ®, 1% Tromethamine, 5% Glycerin, 3% *Calendula*, 0.5% orange fragrance |
| 8 | 140776: 5% Isopropyl alcohol. 50% Labrasol ®, 2% Tween 80 ®, 31.50% Water, 1% Lipacide C8G ®, 1% Lipacide UG ®, 1% Tromethamine, 5% Glycerin, 3% *Calendula*, 0.5% orange fragrance |
| 9 | 140777: 10% Isopropyl alcohol, 60% Labrasol ®, 2% Tween 80 ®, 16.50% Water, 1% Lipacide C8G ®, 1% Lipacide UG ®, 1% Tromethamine, 5% Glycerin, 3% *Calendula*, 0.5% orange fragrance |
| 10 | 140778: 5% Isopropyl alcohol. 60% Labrasol ®, 2% Tween 80 ®, 21.50% Water, 1% Lipacide C8G ®, 1% Lipacide UG ®, 1% Tromethamine, 5% Glycerin, 3% *Calendula*, 0.5% orange fragrance |

Figure 4:
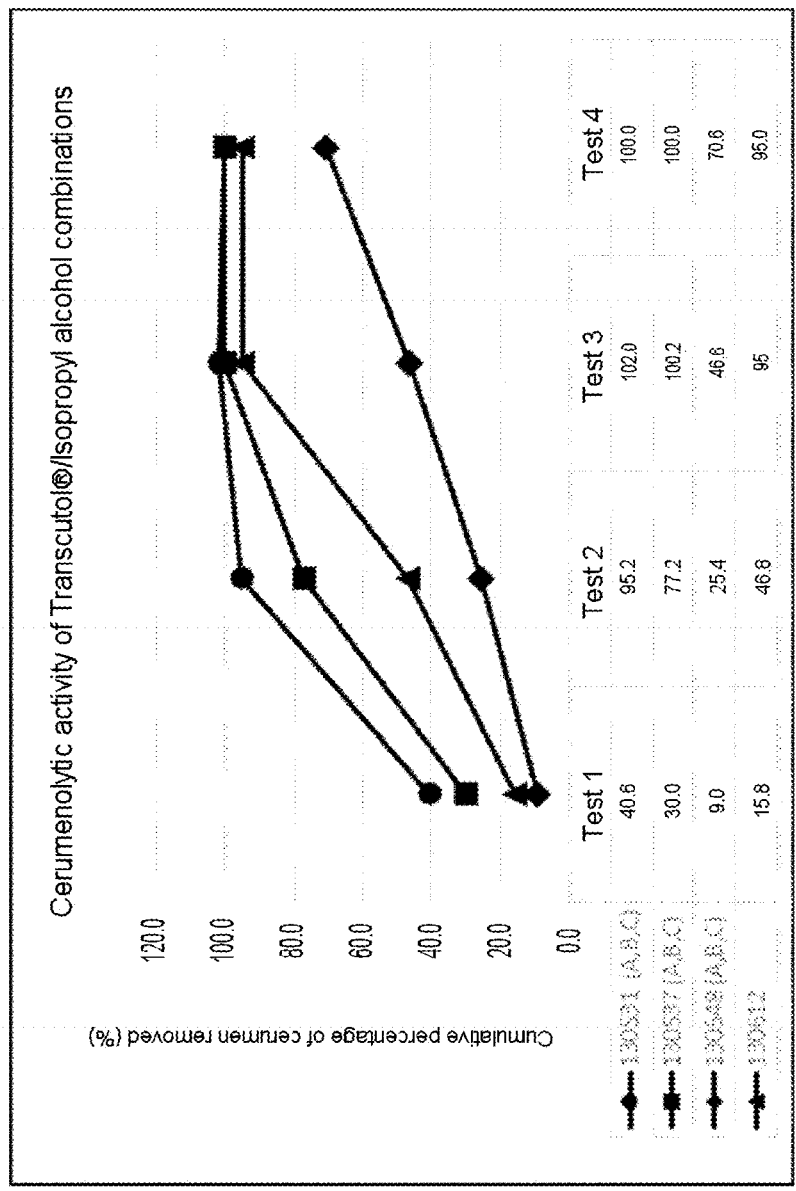

FIG. 4: Graph representing the cerumenolytic effect of the auricular cleaning compositions based on the Transcutol®/isopropyl alcohol combination:

| | |
|---|---|
| 1 | 130531: 40% Isopropyl alcohol; 30% Transcutol ®; 2% Tween 80 ®; 17% Water; 1% Lipacide UG ®; 1% Lipacide C8G ®; 1% Tromethamine; 5% glycerin; 3% *calendula* |
| 2 | 130537: 33% Isopropyl alcohol; 22% Transcutol ®; 2% Tween 80 ®; 33% Water; 1% Lipacide UG ®; 1% Lipacide C8G ®; 1% Tromethamine; 5% glycerin; 3% *calendula* |

-continued 3  130548: 22% Isopropyl alcohol: 14% Transcutol ®; 2% Tween 80 ®; 51% Water; 1% Lipacide UG ®; 1% Lipacide C8G ®; 1% Tromethamine; 5% glycerin; 3% *calendula*
4  130612: 22% Isopropyl alcohol: 33% Transcutol ®; 2% Tween 80 ®; 27% Water; 1% Lipacide UG ®; 1% Lipacide C8G ®; 1% Tromethamine; 10% glycerin; 3% *calendula*

Figure 5:
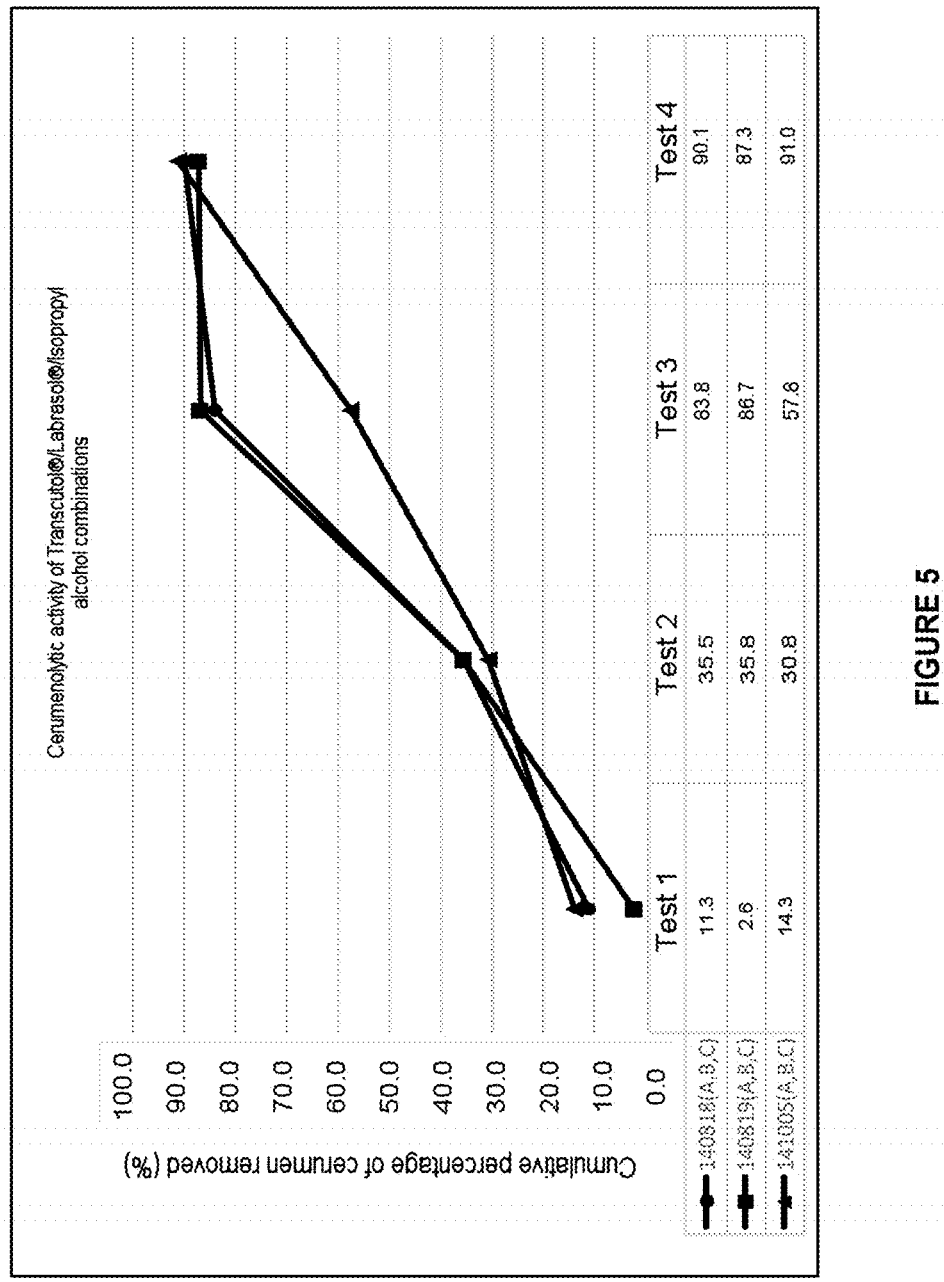

FIG. 5: Graph representing the cerumenolytic effect of the auricular cleaning compositions based on the Transcutol®/isopropyl alcohol/Labrasol® triple combination:

1  140818: 30% Transcutol ®, 35% Labrasol ®, 5% Isopropyl alcohol, 2% Tween 80 ®, 17.0% Water, 1% Lipacide C8G ®, 1% Lipacide UG ®, 1% Tromethamine, 5% Glycerin, 3% *Calendula*
2  140819: 30% Transcutol ®, 30% Labrasol ®, 10% Isopropyl alcohol, 2% Tween 80 ®, 17.0% Water, 1% Lipacide C8G ®, 1% Lipacide UG ®, 1% Tromethamine, 5% Glycerin, 3% *Calendula*
3  140105: 30% Transcutol ®, 20% Labrasol ®, 10% Isopropyl alcohol, 2% Tween 80 ®, 27% Water, 1% Lipacide C8G ®, 1% Lipacide UG ®, 1% Tromethamine, 5% Glycerin, 3% *Calendula*

Figure 6:
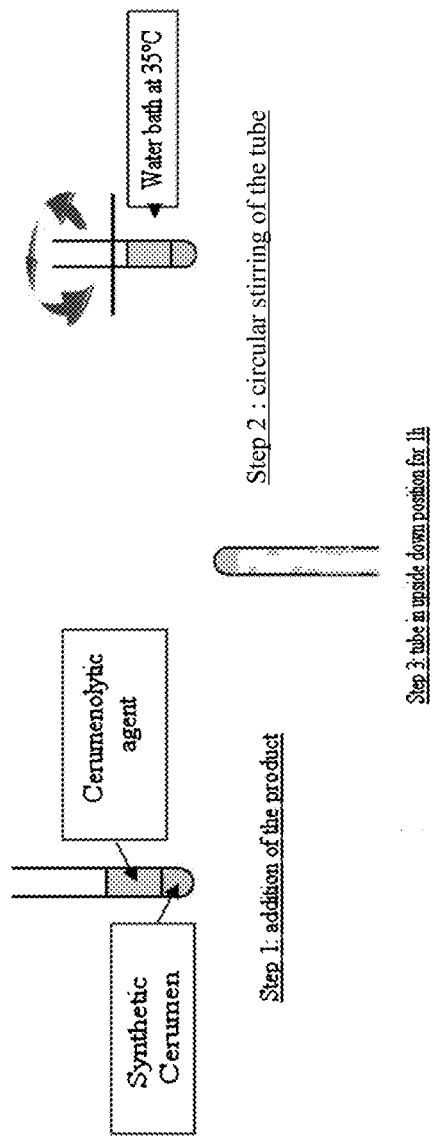

FIG. 6: Diagrammatic illustration of an example of implementation of the procedure of the in vitro cerumenolytic effect test used in example 5.

The following examples are given by way of illustration and cannot be construed as limiting the scope of the invention in any way.

EXAMPLES

In the examples which follow, the term "calendula" used alone refers to a calendula extract sold by the company Chemical&Cosmetic Company Finex (product reference: ZN-02/FX-02, calendula extract diluted to 50% in ethanol).

Example 1: Isopropyl Alcohol/Labrasol® Combination

Figure 1:
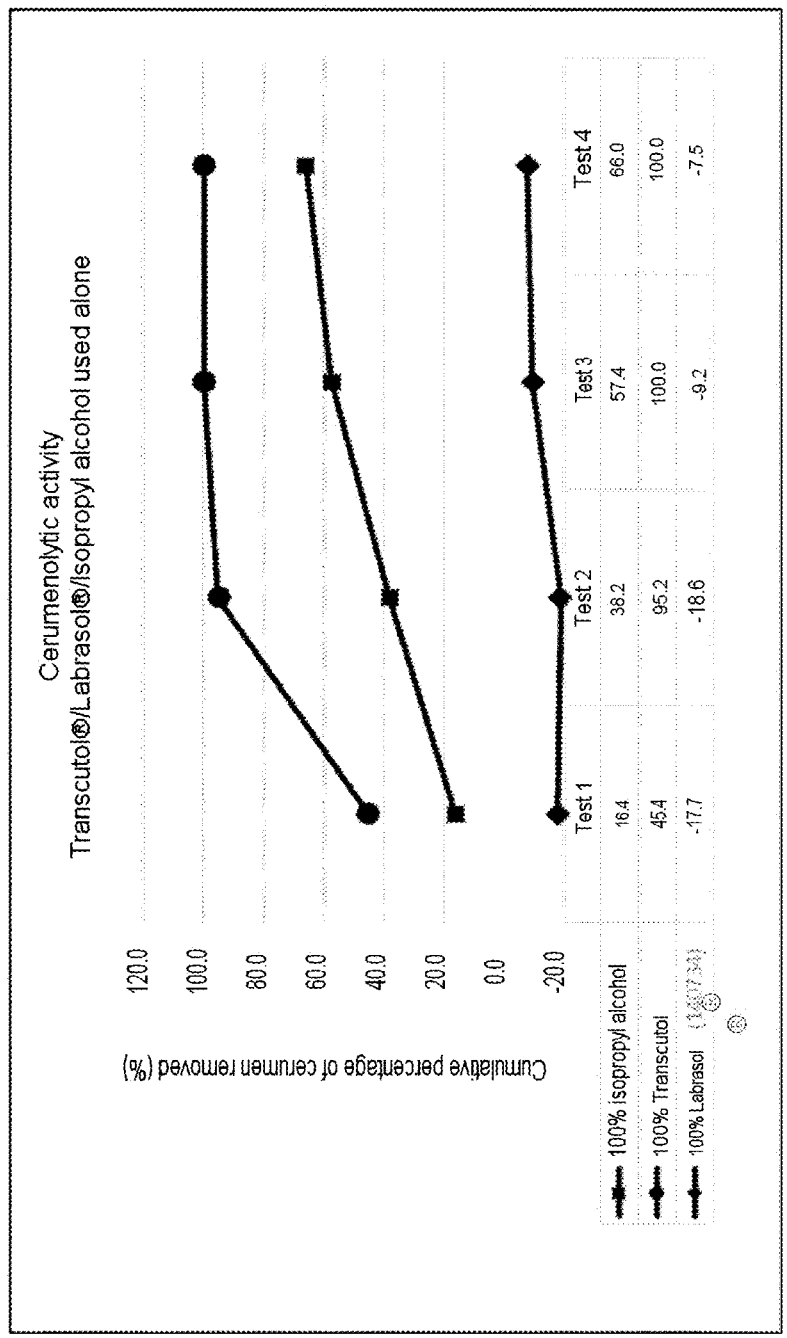
FIG. 1: Graph representing the cerumenolytic effect of the starting materials used alone (isopropyl alcohol, Transcutol® and Labrasol®)

In this example, auricular cleaning compositions were formulated from the following components: Isopropyl alcohol, Labrasol®, Tween 80®, Water, Lipacide C8G®, Lipacide UG®, Tromethamine, Glycerin, Calendula.
The % by weight of each component are indicated in FIG. 1.
The process used is the following:
Mixture 1
In a suitable container, heat the water to 70° C. then add in the following order:
Lipacide C8G®
Lipacide UG®
Tromethamine
Stir for 10 min at 600 rpm
Cool the solution to 40° C. then add:
Tween 80®
Stir for 5 min at 600 rpm
Mixture 2
Incorporate into a suitable container, and in the following order:
Labrasol®
Isopropyl alcohol
Stir for 5 min at 600 rpm
Add mixture 1
Stir for 5 min at 600 rpm
Add in the following order:
Glycerin
Calendula extract
Stir for 5 min at 600 rpm Example 2: Transcutol®/Isopropyl Alcohol Combination In this example, auricular cleaning compositions were formulated from the following components: Transcutol®, Isopropyl alcohol, Tween 80®, Water, Lipacide C8G®, Lipacide UG®, Tromethamine, Glycerin, Calendula.
The % by weight of each component are indicated in FIG. 2.
The process used is the following:
In a suitable container, heat the water to 70° C. then add in the following order:
Lipacide C8G®
Lipacide UG®
Tromethamine
Stir for 10 min at 600 rpm
Cool the solution to 40° C. then add:
Tween 80®
Stir for 5 min at 600 rpm
Add in the following order:
Transcutol®
Isopropyl alcohol
Stir for 5 min at 600 rpm
Add in the following order:
Glycerin
Calendula extract
Stir for 5 min at 600 rpm Example 3: Transcutol®/Labrasol® Combination In this example, auricular cleaning compositions were formulated from the following components: Transcutol®, Labrasol®, Tween 80®, Water, Lipacide C8G®, Lipacide UG®, Tromethamine, Glycerin, Calendula.
The % by weight of each component are indicated in FIG. 3.
The process used is the following:
Mixture 1
In a suitable container, heat the water to 70° C. then add in the following order:
Lipacide C8G®
Lipacide UG®
Tromethamine
Stir for 10 min at 600 rpm
Cool the solution to 40° C. then add:
Tween 80®
Stir for 5 min at 600 rpm
Mixture 2
Incorporate into a suitable container, in the following order:
Labrasol®
Transcutol®
Stir for 5 min at 600 rpm
Add mixture 1
Stir for 5 min at 600 rpm
Add in the following order:
Glycerin
Calendula extract
Stir for 5 min at 600 rpm Example 4: Transcutol®/Labrasol®/Isopropyl Alcohol Combination In this example, auricular cleaning compositions were formulated from the following compositions: Transcutol®, Labrasol®, Isopropyl alcohol, Tween 80®, Water, Lipacide C8G®, Lipacide UG®, Tromethamine, Glycerin, Calendula.

The % by weight of each component are indicated in FIG. 4.

The process used is the following:

Mixture 1

In a suitable container, heat the water to 70° C. then add in the following order:

Lipacide C8G®
Lipacide UG®
Tromethamine
Stir for 10 min at 600 rpm
Cool the solution to 40° C. then add:
Tween 80
Stir for 5 min at 600 rpm Mixture 2

Incorporate into a suitable container, and in the following order:

Labrasol®
Transcutol®
Isopropyl alcohol
Stir for 5 min at 600 rpm
Add mixture 1
Stir for 5 min at 600 rpm
Add in the following order:
Glycerin
Calendula extract
Stir for 5 min at 600 rpm Example 5: Cerumenolytic Effect In Vitro Study The cerumenolytic effect of an ingredient or of a composition can be demonstrated in vitro, via tests using synthetic cerumens.

In the literature, two in vitro studies have been carried out to evaluate the effectiveness of cerumenolytic products. One was carried out by Nielloud et al. (2004) [8], the other was carried out by Sanchez (2006) [9]. The objective of these studies was to determine the ability of the auricular cleaners to dissolve or disperse cerumen and to prevent the redeposition thereof.

The synthetic cerumen composition, produced for each of the two studies, was different (Table 1).

TABLE I

Composition of the artificial cerumen of the studies by Nielloud et al. [8] and by Sanchez et al. [9]

| LIPIDS | Proportion of lipids in the study by Nielloud et al. [8] | Proportion of lipids in the study by Sanchez et al. [9] |
| --- | --- | --- |
| Lanolin | 30.0% | Absent |
| Palmitic acid | 30.0% | 33.6% |
| Myristic acid | 10.0% | 33.6% |
| Oleic acid | 10.0% | 9.4% |
| Linoleic acid | 10.0% | Absent |
| Paraffin oil | 10.0% | Absent |
| Squalene | Absent | 12.5% |
| Linoleic acid | Absent | 10.0% |
| Cholesterol | Absent | 10.9% |

Source: (Nielloud et al, 2004 [8]); (Sanchez et al, 2006 [9])

Sanchez et al. consider that cholesterol is an essential lipid, since it is present in the cerumen of all dogs; however, Nielloud et al did not take it into account. Likewise, they emphasized that lanolin and paraffin are not among the usual lipids of cerumen. For the record, dog cerumen comprises, in more than 90% of individuals, cholesterol, cholesterol esters, free fatty acids, fatty aldehydes and waxes. Consequently, the cerumen produced by Sanchez et al is the one which is the closest to dog cerumen.

Thus, the selected formula of the synthetic cerumen which makes it possible to evaluate the in vitro cerumenolytic effect of agents is the following:

| Centesimal formula (in % m/m) | Synthetic cerumen |
| --- | --- |
| Palmitic acid | 33.6% |
| Myristic acid | 33.6% |
| Oleic acid | 9.4% |
| Cholesterol | 10.9% |
| Squalene | 12.5% |
| TOTAL | 100.0% |

In order to select a new combination of cerumenolytic agents, the cerumenolytic effect test was employed using the cerumen described in the table above.

During the tests, the cerumenolytic effect of the pure or diluted ingredients was evaluated. Subsequently, the impact of the addition of other ingredients was studied (combination effect: potentiating effect) during these in vitro tests.

During the development of the formula of the auricular cleaner, the inventors noted that:

some ingredients having never been used in auricular cleaners have a cerumenolytic effect that is thus far unknown;

some ingredients which do not have an actual cerumenolytic effect, can potentiate the effect of the cerumenolytic agents studied.

Procedure

The procedures described hereinafter set out the various steps of the implementation of the test.

Production and Distribution of Synthetic Cerumen

Before carrying out the tests to evaluate the cerumenolytic effect of pure, diluted or combined agents, it is necessary to produce synthetic cerumen. The procedure is described in the following table:

TABLE 2

| Steps | Parameters | Batch 140636 |
| --- | --- | --- |
| Mixture 1: | Stirring speed | 500 rpm |
| Myristic acid + Palmitic acid | Stirring time | 30 min |
| | Temperature | 65° C. |
| Mixture 2: | Stirring speed | 500 rpm |
| Squalene + Oleic acid | Stirring time | 5 min |
| | Temperature | ambient |
| Mixture 3: | Stirring speed | 500 rpm |
| Mixture 2 + Cholesterol | Stirring time | 5 min |
| | Temperature | ambient |
| Mixture 4: | Stirring speed | 500 rpm then 1000 rpm |
| Mixture 3 + Mixture 1 | Stirring time | 25 min |
| | Temperature | 65° C. |

Once the production has ended, the synthetic cerumen is distributed, while hot, into 10 mm×75 mm test tubes. 500 mg of cerumen are deposited at the bottom of each tube. The distribution is carried out in such a way that the cerumen is present only in the bottom of the tube and not on the edges or the opening, which could distort the results.

The tubes are then left to stand for the amount of time required for the cerumen to solidify. The distribution is carried out the day before the in vitro test in order to leave the cerumen with a minimum of 24 h to cool and solidify.

In Vitro Test Procedure

Following the production of the synthetic cerumen, and the preparation of the pure or diluted agents and the combinations, the in vitro test could thus be carried out.

The dimensions of the test tube, the temperature at which the test was carried out and the amount of synthetic cerumen were chosen to represent as faithfully as possible, in vitro, the dog ear canal.

According to these parameters, the procedure followed for measuring the in vitro effectiveness of an agent or of a combination of agents having a cerumenolytic effect is the following:

The test tube containing only the cerumen is weighed before the test.

Then, 2 ml of test product is removed using a pipette and is then deposited on top of the cerumen.

The test tube is then attached to a stirring turbine and immersed in a bath of water heated to 35° C. (the water height is sufficient for the content of the tube (cerumen+test product) to be immersed.

The stirring is maintained for 20 minutes at 50 rpm.

After the stirring has been stopped, the tube is removed form the turbine of the water bath at 35° C. and is then placed upside down for 1 h. This step makes it possible to remove the product and the cerumen debris detached by the cerumenolytic agent.

At the end of the time elapsed, the tube is weighed to evaluate the amount of cerumen removed.

This process is carried out four times in a row, on each same tube, in order to simulate and evaluate the application number required to remove the cerumen plug present in the dog ear canal.

Each time, the cerumen remaining at the bottom of the tube is dried and then weighed. For the next application, 2 ml of product are again added to the remaining cerumen bed and the steps described above are begun again.

The implementation of the main steps of the test can be represented diagrammatically as indicated in FIG. 6.

Measurement of Cerumenolytic Effect in Vitro

As previously indicated, in order to check the effectiveness of an agent, the test tubes are weighed before the test is carried out and after the phase of leaving to stand upside down for 1 h.

The removal of the cerumen is, according to this process, evaluated as for this example:

Weight of the tube A before test 1: 3.493 g and weight of the tube A after test 1: 3.449 g Percentage of cerumen removed: (3.493−3.449)/0.5× 100=8.8%.

According to test 1, formula A used in the tube A made it possible to remove a part of the cerumen. The percentage as indicated is 8.8%.

The percentages are thus calculated for each test: from 1 to 4. The total percentage of cerumen removed is obtained after having repeated the operation successively four times for one and the same tube.

From the in vitro cerumenolytic tests, an excipient not known for its cerumenolytic effect was identified as having a very marked cerumenolytic activity: diethylene glycol monoethyl ether.

The latter is used as solvent for an injectable product or a product for topical, dermatological or transdermal applications. As illustrated in FIG. 1, a solution containing 100% of Transcutol® (diethylene glycol monoethyl ether) has a cerumenolytic activity close to 100%.

It was also noted that some ingredients, such as caprylocaproyl macrogol-8 (or caprylcaproyl polyoxyl-8 glyceride) known for its surfactant and solubilizing activities, can be a potentiator of a cerumenolytic effect for other cerumenolytic agents.

Caprylocaproyl macrogol-8 does not have a cerumenolytic effect as such. Indeed, the results of the in vitro test show that its cerumenolytic activity is close to zero (cf. FIG. 1).

The potentiating effect was shown in combination with isopropyl alcohol and also in combination with diethylene glycol monoethyl ether.

The results of the in vitro tests show that a solution of isopropyl alcohol (100% alcohol) has a cerumenolytic effect of about 60% (cf. FIG. 1). The latter diluted with hydrophilic products, for example 25% alcohol+75% water, experiences a significant reduction in cerumenolytic activity which is close to zero in certain cases. On the other hand, the addition of caprylocaproyl macrogol-8 to these compositions potentiates the cerumenolytic effect of dilute isopropyl alcohol, which reaches efficiencies close to 90% (see tables below).

TABLE 3

| Compositions tested | % of cerumen removed |
|---|---|
| 100% Isopropyl alcohol | 66 |
| 100% Transcutol ® | 100 |
| 100% Labrasol ® | −7.5 |
| 25% Isopropyl alcohol; 75% Water | −4.6 |
| 40% Isopropyl alcohol; 2% Tween 80 ®; 47% Water; 1% Lipacide UG ®; 1% Lipacide C8G ®; 1% Tromethamine;5% Glycerin;3% *calendula* | 75.2 |
| 20% Isopropyl alcohol;2% Tween 80 ®;66.50% Water; 1% Lipacide C8G ®; 1% Lipacide UG ®; 1% Tromethamine; 5% Glycerin; 3% *Calendula*; 0.5% orange fragrance | 30.9 |
| 20% Isopropyl alcohol; 40% Labrasol ®; 2% Tween 80 ®; 26.50% Water; 1% Lipacide C8G ®; 1% Lipacide UG ®; 1% Tromethamine; 5% Glycerin; 3% *Calendula*; 0.5% orange fragrance | 95.6 |
| 15% Isopropyl alcohol; 50% Labrasol ®; 2% Tween 80 ®; 21.50% Water; 1% Lipacide C8G ®; 1% Lipacide UG ®; 1% Tromethamine; 5% Glycerin; 3% *Calendula*; 0.5% orange fragrance | 82.1 |
| 15% Isopropyl alcohol; 60% Labrasol ®; 2% Tween 80 ®; 11.50% Water; 1% Lipacide C8G ®; 1% Lipacide UG ®; 1% Tromethamine; 5% Glycerin; 3% *Calendula*; 0.5% orange fragrance | 87.5 |
| 10% Isopropyl alcohol; 60% Labrasol ®; 2% Tween 80 ®; 16.50% Water; 1% Lipacide C8G ®; 1% Lipacide UG ®; 1% Tromethamine; 5% Glycerin; 3% *Calendula*; 0.5% orange fragrance | 75.9 |
| 10% Isopropyl alcohol; 50% Labrasol ®; 2% Tween 80 ®; 26.50% Water; 1% Lipacide C8G ®; 1% Lipacide UG ®; 1% Tromethamine; 5% Glycerin; 3% *Calendula*; 0.5% orange fragrance | 77.5 |
| 5% Isopropyl alcohol; 50% Labrasol ®; 2% Tween 80 ®; 31.50% Water; 1% Lipacide C8G ®; 1% Lipacide UG ®; 1% Tromethamine; 5% Glycerin; 3% *Calendula*; 0.5% orange fragrance | 59.3 |

The same phenomenon is observed in combination with diethylene glycol monoethyl ether (cf. Table 4).

TABLE 4

| | % cerumen removed (after test 4) |
|---|---|
| 100% Transcutol ® | 100.0 |
| 100% Labrasol ® | −7.5 |
| 50% Transcutol ®/50% Water | −7.4 |
| 40% Transcutol ®, 30% Labrasol ®, 2% Tween 80 ®, 17.0% Water, 1% Lipacide C8G ®, 1% Lipacide UG ®, 1% Tromethamine, 5% Glycerin, 3% Calendula | 93.8 |
| 30% Transcutol ®, 40% Labrasol ®, 2% Tween 80 ®, 17.0% Water, 1% Lipacide C8G ®, 1% Lipacide UG ®, 1% Tromethamine, 5% Glycerin, 3% Calendula | 65.6 |
| 30% Transcutol ®, 30% Labrasol ®, 2% Tween 80 ®, 27.0% Water, 1% Lipacide C8G ®, 1% Lipacide UG ®, 1% Tromethamine, 5% Glycerin, 3% Calendula | 32.1 |
| 30% Transcutol ®, 20% Labrasol ®, 2% Tween 80 ®, 37.0% Water, 1% Lipacide C8G ®, 1% Lipacide UG ®, 1% Tromethamine, 5% Glycerin, 3% Calendula | 17.3 |

Example 6: Comparative Cerumenolytic Test in Vivo

Controlled Double-Blind Randomized Clinical Study

A comparative study was carried out in order to evaluate the cleaning effectiveness of an ear composition according to the invention, compared with that of a reference veterinary product (Epi-Otic®), which is a reference product on the market for the intended application (auricular cleaner).

The auricular cleaning composition according to the invention tested in this example uses the triple combination of isopropyl alcohol with diethylene glycol monoethyl ether as cerumenolytic agent(s), in combination with caprylcaproyl polyoxyl-8 glyceride.

This test composition was compared with the reference product Epi-Otic® from the company Virbac, in terms of external ear canal cleaning effectiveness, on dogs suffering from spontaneous external otitis. The cleaning product (test sample or reference sample) was dedicated to cleaning the walls of the external ear canal of the animals, in order to prepare the ear to receive the therapeutic treatment suitable for treating the external otitis.

The study carried out was a controlled double-blind randomized clinical study, that is to say that the owners who administered the product (reference product or test composition according to the invention) to their dog and the veterinarian who evaluated the clinical data (ear cytology and video-otoscopic examination) were operating blind. The samples (composition according to the invention or Epi-Otic®) were identified by a code, the list and the identity of which were disclosed only after the clinical study. Each sample was administered randomly according to a randomization list.

After an initial examination of the external ear canal of the animal, the cleaning product was administered and, 30 minutes later, a video-otoscopic follow-up examination was carried out and samples for the cytology were collected using swabs, in order to evaluate the cleaning effectiveness and the cerumenolytic effect of the products.

Briefly, the amount of cerumen present in the external ear canal of each animal was determined by video-otoscopy, 30 minutes after the first application of the cleaning product (test sample according to the invention, or Epi-Otic® reference sample). The amount of wax in the ear (cerumen) was evaluated using a score sheet (from 0 to 4):

0: absence of cerumen;

1: a few small thin plaques of cerumen which adhere to the wall of the ear canal;

2: several plaques of cerumen of various thicknesses. Only a slight coalescence of the cerumen plaques adhering to the wall of the ear canal is observed. No ceruminolith;

3: many thick, often coalescent, plaques of cerumen, which adhere to the wall of the ear canal. Possible presence of ceruminoliths;

4: the wall of the ear canal is virtually completely covered with cerumen.

The median for the ear wax score was 6 for the cleaning products used immediately before the first application of the sample, this being both for the dogs receiving the test product according to the present invention, and for those receiving the Epi-Otic® reference product (the score of 6 corresponds to a dirty starting ear, before the initiation of the study and any application of cleaning product). The dogs used in the study therefore all had the same starting cerumen base, namely dirty ears. The evaluation at +30 minutes showed that the median for the test product according to the invention was 3, whereas it was 4 for the Epi-Otic® reference product (cf. Table 5 below). This difference is significant (Wilcoxon test, p=0.004).

TABLE 5

Results of the scores relating to the amount of cerumen present in the external ear canal of the animals

| Score before application of the cleaning product ($T_0$) Value P (p < 0.01) | $T_0$ + 30 minutes |
|---|---|
| Test product according to the invention (Median = 6) | 0.001 (Median = 3) |
| Reference product (Epi-Otic ®) (Median = 6) | 0.001 (Median = 4) |

The results of this study revealed that the test composition according to the invention showed a significantly greater cleaning capacity than the reference product (Epi-Otic®). There was no significant difference in the cytological grading between the reference product (Epi-Otic®) and the test samples (composition according to the invention). However, the video-otoscopic examination showed that, 30 minutes after the administration with the sample of cleaning product, the remaining amount of cerumen in the external ear canal of the animals was significantly lower in the animals that had received the test product according to the present invention.

The test product (composition according to the invention) was moreover well tolerated by all the dogs, no major adverse event was observed; and the assessment of the test product by the owners of the dogs was: "very good product".

In summary, the test product (composition according to the invention) proved to be comparable to the Epi-Otic® reference product in terms of tolerance, but showed a significantly greater cleaning effectiveness than that of Epi-Otic®. Indeed, the test product according to the present invention removes a large part of the cerumen after 30 minutes following the first application, which is not the case with Epi-Otic®.

REFERENCE LIST

1. HAWKE M., "*Update on cerumen and cerumenolytic s*". Ear, Nose & Throat Journal, 2002, 81 (8 Suppl 1), p23-24.
2. MALARD O., BEAUVILLAIN de MONTREUIL C, LEGENT F. "*Pathologie acquise de l'oreille externe*" ["*Acquired pathology of the outer ear*"]. Oto-rhino-laryngologie, published by Masson, 20-070-A10, 2005.
3. U.S. Pat. No. 3,422,186
4. U.S. Pat. No. 4,895,875
5. U.S. Pat. No. 5,296,472
6. U.S. Pat. No. 5,380,711
7. U.S. Pat. No. 5,480,658
8. Nielloud et al., "P-75 Development of an in vitro test to evaluate cerumen-dissolving properties of veterinary ear cleansing solutions", Veterinary Dermatology, vol 15, issue supplement s 1, August 2004, p 65.
9. Sanchez et al., «In vitro investigation of cerumenolytic activity of various otic cleaners for veterinary use" Veterinary Dermatology, vol 17, N° 2, April 2006, p 121-127.

The invention claimed is:

1. A process for potentiating the cerumenolytic effect of isopropyl alcohol and/or of diethylene glycol monoethyl ether in an auricular cleaning composition, comprising combining isopropyl alcohol and/or diethylene glycol monoethyl ether with an amount of caprylcaproyl polyoxyl-8 glyceride effective to potentiate cerumenolytic effects of the isopropyl alcohol and/or diethylene glycol monoethyl ether to obtain an auricular cleaning composition, wherein the amount of caprylcaproyl polyoxyl-8 glyceride in the auricular cleaning composition is 20% to 60% by weight of the auricular cleaning composition.

2. The process of claim 1, wherein the auricular cleaning composition comprises:
   diethylene glycol monoethyl ether and isopropyl alcohol in combination with caprylcaproyl polyoxyl-8 glyceride.

3. The process of claim 2, wherein the auricular cleaning composition further comprises an otologically acceptable aqueous carrier.

4. The process of claim 1, wherein the auricular cleaning composition comprises
   a diethylene glycol monoethyl ether content ranging from 25% to 35% by weight,
   an isopropyl alcohol content ranging from 5% to 10% by weight, and
   a caprylcaproyl polyoxyl-8 glyceride content ranging from 20% to 35% by weight;
   the total content of diethylene glycol monoethyl ether, isopropyl alcohol and caprylcaproyl polyoxyl-8 glyceride ranging from 60% to 70% by weight;
   the % being expressed relative to the total weight of the auricular cleaning composition.

5. The process of claim 4, wherein the auricular cleaning composition comprises an otologically acceptable aqueous carrier.

6. The process of claim 1, wherein the auricular cleaning composition further comprises an anti-seborrheic agent, an emollient, a surfactant, a buffering agent, an antiseptic agent, and an anti-inflammatory agent.

7. The process of claim 6, wherein the auricular cleaning composition further comprises a preservative.

8. The process of claim 6, wherein:
   the anti-seborrheic agent is undecylenoyl glycine;
   the emollient is glycerin;
   the surfactant is a polysorbate;
   the buffering agent is trishydroxymethylaminomethane;
   the antiseptic agent is a calendula extract; and
   the anti-inflammatory agent is a calendula extract.

9. The process of claim 8, wherein the auricular cleaning composition further comprises a preservative.

10. The process of claim 8, wherein the calendula extract comprises a marigold extract.

11. The process of claim 1 wherein the auricular cleaning composition comprises
    10% to 40% by weight diethylene glycol monoethyl ether, and/or
    5% to 20% by weight isopropyl alcohol,
    the % being expressed relative to the total weight of the auricular cleaning composition.

* * * * *